(12) United States Patent
Platica

(10) Patent No.: US 9,062,350 B2
(45) Date of Patent: Jun. 23, 2015

(54) METHOD OF MUTATION DETECTION IN BLOOD CELL-FREE DNA USING PRIMER EXTENSION (PE) AND PCR

(71) Applicant: Ovidiu Platica, New York, NY (US)

(72) Inventor: Ovidiu Platica, New York, NY (US)

(73) Assignee: U.S. Department of Veterans Affairs, Washington, DC (US)

( * ) Notice: Subject to any disclaimer, the term of this patent is extended or adjusted under 35 U.S.C. 154(b) by 0 days.

(21) Appl. No.: 13/792,423

(22) Filed: Mar. 11, 2013

(65) Prior Publication Data

US 2014/0093872 A1    Apr. 3, 2014

Related U.S. Application Data

(60) Provisional application No. 61/707,905, filed on Sep. 29, 2012.

(51) Int. Cl.
*C12Q 1/68* (2006.01)

(52) U.S. Cl.
CPC ........ *C12Q 1/6886* (2013.01); *C12Q 2600/156* (2013.01)

(58) Field of Classification Search
None
See application file for complete search history.

(56) References Cited

U.S. PATENT DOCUMENTS

2006/0099607 A1* 5/2006 Nakashima et al. ............... 435/6

OTHER PUBLICATIONS

Platica et al. (PE-PCR, a novel method for detection of mutations in blood-cell-free DNA, J Clin Oncol 30, 2012 (suppl; abstr e12016), presented at ASCO Annual Meeting and available online May 17, 2012).*
Nakamoto et al. (Detection of Tumor DNA in Plasma Using Whole Genome Amplification, Bull Tokyo Dent Coll, (2006) 47(3); 125-131).*
Li et al. (Whole Genome Amplification of Plasma-Circulating DNA Enables Expanded Screening for Allelic Imbalance in Plasma, Journal of Molecular Diagnostics, vol. 8, No. 1, Feb. 2006).*
Sorenson et al. (Soluble Normal and Mutated DNA Sequences from Single-Copy Genes in Human Blood, Cancer Epidemiol Biomarkers Prev, 1994;3:67-71).*
Ariga et al. (Kinetics of fetal cellular and cell-free DNA in the maternal circulation during and after pregnancy: implications for noninvasive prenatal diagnosis, Transfusion, vol. 41, Dec. 2001).*
Nigam et al. (Detection of Fetal Nucleic Acid in Maternal Plasma: A Novel Noninvasive Prenatal Diagnostic Technique, JIMSA Jul.-Sep. 2012 vol. 25 No. 3).*
Phylipsen et al. (Non-invasive prenatal diagnosis of beta-thalassemia and sickle-cell disease using pyrophosphorolysis-activated polymerization and melting curve analysis, Prenatal Diagnosis, Apr. 20, 2012, 32, 578-587).*
Liu et al. (Pyrophosphorolysis-Activated Polymerization (PAP): Application to Allele-Specific Amplification, BioTechniques 29:1072-1083 (Nov. 2000)).*
Liu & Sommer (hereinafter "Liu2"; Detection of extremely rare alleles by bidirectional pyrophosphorolysis-activated polymerization allele-specific amplification (Bi-PAP-A): measurement of mutation load in mammalian tissues, BioTechniques 36:156-166 (Jan. 2004)).*
Boon et al. (Y chromosome detection by Real Time PCR and pyrophosphorolysis-activated polymerisation using free fetal DNA isolated from maternal plasma, Prenat Diagn 2007; 27: 932-937, Published online Jun. 29, 2007).*
Hosono et al. (Unbiased Whole-Genome Amplification Directly From Clinical Samples, Genome Res. May 13, 2003;13(5):954-64. Epub Apr. 14, 2003).*
Fernando et al. (A new methodology to preserve the original proportion and integrity of cell-free fetal DNA in maternal plasma during sample processing and storage, Prenat Diagn 2010; 30: 418-424, Published online Mar. 19, 2010).*
Oldenburg et al. (Selective Amplification of Rare Mutations Using Locked Nucleic Acid Oligonucleotides that Competitively Inhibit Primer Binding to Wild-Type DNA, Journal of Investigative Dermatology (2008) 128, 398-402).*
Handyside et al. (Isothermal whole genome amplification from single and small numbers of cells: a new era for preimplantation genetic diagnosis of inherited disease, Molecular Human Reproduction vol. 10, No. 10 pp. 767-772, 2004, Advance Access publication Aug. 20, 2004).*
Vestheim et al. (Blocking primers to enhance PCR amplification of rare sequences in mixed samples—a case study on prey DNA in Antarctic krill stomachs, Frontiers in Zoology, Jul. 20, 2008, 5:12).*
Orou et al. (Allele-Specific Competitive Blocker PCR: A One-Step Method With Applicability to Pool Screening, Human Mutation 6:163-169 (1995)).*
Dominguez et al. (Wild-type blocking polymerase chain reaction for detection of single nucleotide minority mutations from clinical specimens, Oncogene (2005) 24, 6830-6834).*
Dabritz et al. (Detection of Ki-ras mutations in tissue and plasma samples of patients with pancreatic cancer using PNA-mediated PCR clamping and hybridisation probes, British Journal of Cancer (2005) 92, 405-412).*
Milbury et al. (PCR-Based Methods for the Enrichment of Minority Alleles and Mutations, Clin Chem. Apr. 2009; 55(4): 632-640.).*
Nasis et al. (Improvement in Sensitivity of Allele-specific PCR Facilitates Reliable Noninvasive Prenatal Detection of Cystic Fibrosis, Clinical Chemistry 50:4, pp. 1-8 (2004)).*
Vlckova et al. (Comparison of various methods used for extraction of cell-free genomic DNA from human plasma, Klin. Biochem. Metab., 14 (35), 2006, No. 1, p. 21-24).*

(Continued)

*Primary Examiner* — Stephanie K Mummert
*Assistant Examiner* — Aaron Priest
(74) *Attorney, Agent, or Firm* — Dinesh Agarwal, P.C.

(57) ABSTRACT

A method of detecting mutation in blood cell-free DNA, includes providing a serum sample, isolating DNA from the serum sample, amplifying the DNA by polymerase chain reaction (PCR), subjecting the PCR product to primer extension (PE), and separating the PE reaction product and identifying the mutation by gel electrophoresis. In order to improve accuracy and sensitivity, the PE reaction can be carried out by using a primer that blocks the extension of the wild or non-mutated sequence.

23 Claims, 4 Drawing Sheets

(56) References Cited

OTHER PUBLICATIONS

Wright et al. (The use of cell-free fetal nucleic acids in maternal blood for non-invasive prenatal diagnosis, Human Reproduction Update, vol. 15, No. 1 pp. 139-151, 2009, Advanced Access publication on Oct. 22, 2008).*

Cabral et al. (Circulating DNA as a Biomarker for Early Detection of Cancer: A Brief Update with an Emphasis on Lung Cancer, The Open Lung Cancer Journal, 2010, 3, 38-44).*

Anker et al. (Detection of circulating tumour DNA in the blood (plasma/serum) of cancer patients, Cancer and Metastasis Reviews 18: 65-73, 1999).*

Li et al. (Size Fractionation of Cell-Free DNA in Maternal Plasma and Its Application in Noninvasive Detection of Fetal Single Gene Point Mutations, in Methods in Molecular Biology, vol. 444: Prenatal Diagnosis, Ch. 19, pp. 239-251, 2008).*

* cited by examiner

Ext primer (PE)
CACATGACGGAGGTTGTGAGGCActgccccctgg-3' (SEQ ID NO: 5)

P53 Mutated seq
5'-TGTCGTGTACTGCCTCCAACACTCCGTGACGGGGGAC (SEQ ID NO: 6)

FIGURE 1A

Ext primer (PE)
CACATGACGGAGGTTGTGAGGCA......... (SEQ ID NO: 7)

P53 wild seq
5'-TGTCGTGTACTGCCTCCAACACTCCGCGACGGGGGAC (SEQ ID NO: 8)

FIGURE 1B

Blocking primer (PE)
CACATGACGGAGGTTGTGAGGCGddNTP......... (SEQ ID NO: 9)

P53 wild seq
TGTCGTGTACTGCCTCCAACACTCCGCGACGGGGGAC (SEQ ID NO: 8)

FIGURE 2

"Tail" Primer
5'-TGCACGAGGATGCTATCAAGG-3' (SEQ ID NO: 10)

FIGURE 3

```
                        SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tctgtctttg ctgcctcttc t                                                 21

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
agagcaatca gtgaggaatc ag                                                22

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccttcctctt cctacagtac t                                                 21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gaatcagtga ggaatcagag                                                   20

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
```

```
cacatgacgg aggttgtgag gcactgcccc tgg                                    33

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgtcgtgtac tgcctccaac actccgtgac gggggac                                37

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cacatgacgg aggttgtgag gca                                               23

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tgtcgtgtac tgcctccaac actccgcgac gggggac                                37

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(24)
<223> OTHER INFORMATION: dideoxynucleotide triphosphate

<400> SEQUENCE: 9
cacatgacgg aggttgtgag gcgn                                              24

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tgcacgagga tgctatcaga a                                                 21
```

METHOD OF MUTATION DETECTION IN BLOOD CELL-FREE DNA USING PRIMER EXTENSION (PE) AND PCR

CROSS-REFERENCE TO RELATED APPLICATIONS

The present application claims priority on prior U.S. Provisional Application Ser. No. 61/707,905, filed Sep. 29, 2012, which is hereby incorporated herein in its entirety by reference.

REFERENCE TO SEQUENCE LISTING

The present application contains a Sequence Listing (SEQ ID No:1 to SEQ ID No: 10), which has been submitted in ASCII format via EFS-Web and is hereby incorporated by reference in its entirety. Said ASCII copy, created on May 2, 2013, is named US1603-13_SL.txt and is 2,744 bytes in size.

STATEMENT REGARDING FEDERALLY SPONSORED RESEARCH OR DEVELOPMENT

The work leading to the present invention was made with Government support, and specifically by an employee of the U.S. Department of Veterans Affairs. The U.S. Government, therefore, has certain rights in the invention.

FIELD AND BACKGROUND OF THE INVENTION

The present invention is generally directed to cancer diagnosis or prognosis, and more particularly to the detection of mutation(s) in blood cell-free DNA using primer extension and PCR.

The presence of abnormally high levels of cell-free blood DNA (CFDNA) in the plasma/serum of cancer patients was demonstrated in 1977. However, it is only recently that CFDNA in cancer has attracted attention and that its possible use as a marker for diagnosis or prognosis has been investigated. Mutations in CFDNA have been characterized in a large variety of cancer types and sites, including, for example, colorectal, pancreas, lung, bladder, head and neck and liver cancers. Various types of DNA alterations have been reported in CFDNA, including point mutations, DNA hypermethylations, microsatellite instabilities and losses of heterozygosity. In many instances, these alterations were identical to the ones found in the primary tumor tissue of the patient, supporting the tumoral origin of altered CFDNA.

Occurrence of alterations in CFDNA, as well as increase in the overall level of CFDNA, is not restricted to any particular tumor site, type or grade. However, there is tendency for significantly larger amounts of CFDNA in patients with late stage disease and metastasis. Thus, CFDNA may provide a very valuable source of genetic material as a surrogate for molecular analysis in cancer and pre-cancer patients. CFDNA could be an alternate to tissue biopsy and provide an easily accessible and non-invasive modality to determine the genetic background of materials.

The detection of CFDNA is not without challenges. Tumor DNA is present at very low concentrations in the blood. In addition, the mutation detection should be carried out in the presence of a very large excess of normal homologous DNA. The excess of homologous sequences interfaces with mutation detection by sequencing when mutated DNA is less than 5 percent because the signal from mutated nucleotide will be completely masked by homologous nucleotides from normal DNA. Since the majority of mutation detection techniques are based on sequencing, such methods are not adequate for blood DNA samples. In addition, whole genome sequencing is not applicable either for DNA mutation detection because it requires the sequencing of hundreds of normal genomes to find the mutated genome.

In addition, the modern approach for treatment of cancer known as "personalized medicine" relies on identification of the genetic traits, normal and abnormal, which determines the particular behavior of the same disease in different patients. Based on this information an individualized management can be devised to ensure maximum of benefit with minimum risk for patients.

An integral component of personalized medicine is the targeted therapy aimed at overcoming the effect of specific molecular alterations in an individual tumor.

To ensure the benefit of targeted therapy, testing for mutations in several genes has become a basic requirement. This testing is usually performed on tissue specimen obtained by biopsy at initial diagnosis. However, frequently the amount of biopsy specimen is not sufficient for these studies or diagnosis is made by thin needle aspirates or by cytology, which make the genetic studies very difficult or impossible.

Another difficulty in genetic studies is the frequent contamination of tumoral specimen with normal cells. In such cases, either the patient accepts the inconvenience of a second biopsy or he/she will not benefit from the targeted therapy.

About 40-years ago, it was shown that tumoral, as well as normal cells release their DNA in blood in high molecular weight form and that this nucleic acid caries the same molecular alterations as the cells of origin.

As noted above, the blood cell-free DNA (BCF DNA or CFDNA) has become an attractive source of genetic information, provided an adequate technology is available to bring such data to the clinician. However, the identification of such alterations in blood is difficult because the tumoral DNA is found in very low concentration and it is mixed with a large amount of normal homologous DNA.

When compared to the biopsy source, besides being more accessible and convenient to patients, the plasma DNA could also allow identification of genotype changing during progression through emergency of new mutations in cancer cells. These mutations could herald, for instance, the development of drug resistance, and thus, guide timely changes of treatment, or could identify new potential targets for additional therapy.

Some recent preliminary studies indicate that mutations in BCF could be detected very early during the progression of disease when the cancer can be cured with surgical resection.

This is a new and exciting application of BCF DNA with very important implications for cancer patients. At present, only rarely the cytotoxic or targeted therapy can cure a malignancy. In general, the surgical resection and sometimes radiation therapy can cure at least 50% of patients with any solid tumor, provided the disease is localized in the organ of origin. The lower limit of clinical detection of a malignant lesion is usually a nodule of 1 cm diameter. Such nodule contains about $10^9$ cells from most histological type. It is conceivable that nodule smaller than 1 cm and below the limit of clinical detection, and containing a few hundreds of millions of cancer cells, could still release enough mutated DNA which, when detected, would be indicative of the presence of a developing malignancy. Following the detection of such mutation in BCF DNA, the patient could be followed by PET scans every 4-6 months until the nodule is identified. If this nodule is confirmed malignant by biopsy, the patient can have the nodule resected and eventually be cured of cancer.

With this idea in mind I have developed a novel strategy for mutation detection in BCF DNA that is able to detect very low level of mutated genes.

ASPECTS OF THE INVENTION

The present disclosure is directed to various aspects of the present invention.

One aspect of the present invention is to provide a method for detecting very low abundance mutation in cell-free blood DNA.

Another aspect of the present invention is to provide a non-invasive method for detecting cancer, and particularly early tumor growth.

Another aspect of the present invention is to provide a non-invasive method for detecting cancer, especially in situations where the biopsy specimen is inadequate for testing.

Another aspect of the present invention is to provide a non-invasive method for detecting cancer, which is fast, very sensitive, and highly reproducible. More particularly, the method requires 10-20 ul (or less) serum and can be completed in 1-2 days, or less.

Another aspect of the present invention is to provide a method of detecting mutation in blood cell-free DNA, which includes providing a serum/blood sample, isolating DNA from the serum/blood sample, amplifying the DNA by polymerase chain reaction (PCR), subjecting the PCR product to primer extension (PE), and separating the PE reaction product and identifying the mutation by gel electrophoresis.

Another aspect of the present invention is to provide a method of detecting mutation in blood cell-free DNA, which includes providing a serum/blood sample, subjecting the serum/blood sample to whole genome DNA amplification, amplifying the genome DNA by a first polymerase chain reaction (PCR), re-amplifying a portion of the PCR product by a second polymerase chain reaction (PCR), subjecting the second PCR product to primer extension (PE), and separating the PE reaction product and identifying mutation by gel electrophoresis or chemiluminescence.

Another aspect of the present invention is to provide a method of detecting mutation in blood cell-free DNA, which includes providing a serum sample, isolating DNA from the serum/blood sample, amplifying the DNA by polymerase chain reaction (PCR), subjecting the PCR product to primer extension (PE) by using at least one blocking primer as set forth in SEQ ID NO: 9 and an extension primer, and separating the PE reaction product and identifying the mutation by gel electrophoresis.

BRIEF DESCRIPTION OF THE DRAWINGS

One of the above and other aspects, novel features and advantages of the present invention will become apparent from the following detailed description of the non-limiting preferred embodiment(s) of invention, illustrated in the accompanying drawings, wherein:

FIG. 1A shows the extension of a primer for a mutation in codon 175 of P53 gene in a DNA fragment amplified in DNA from ovarian cell line TOV-112D, where the extension has proceeded up to the end of the fragment;

FIG. 1B shows the absence of extension in the DNA lacking the mutation;

FIG. 2 shows a blocking extension primer terminated at 3° end with a dideoxynucleotide triphosphate (SEQ ID NO: 9); and FIG. 3 shows a tail primer (SEQ ID NO: 10).

DETAILED DESCRIPTION OF THE PREFERRED EMBODIMENT(S) OF THE INVENTION

PE-PCR is a novel method for detection of known mutations in blood cell free DNA. It is based on a combination of PCR and primer extension (PE). The mutation detection using PE relies on the property of certain polymerases to extend a primer annealed to a template only when the primer 3' nucleotide is strict complementary to template. In this manner, when the 3' nucleotide is complementary to mutated nucleotide, the primer will be extended that can be detected by gel electrophoresis.

The PE used for this purpose relies on the highly specific enzymatic extension of a gene primer, which encodes the mutated nucleotide at its 3' terminus.

The mutation detection in blood cell free DNA poses a major difficulty; the mutated genome released only from cancer cells, is diluted into a huge amount of normal homologous DNA derived from normal cells. It is estimated that for each mutated genome, there are 1000-10,000 normal genomes in the blood. This huge excess of normal homologous sequences interferes with mutation detection by most available technologies like those based on PCR and sequencing.

Neither PCR or PE, when used separately, can detect mutations in blood DNA. The present method combines PCR and PE in a novel strategy, which can identify such mutations in blood DNA.

This strategy includes an initial amplification of whole genomic CF DNA from 2 ul serum, followed by amplification of a small DNA fragment containing the mutation by nested primer PCR for about 60 cycles. In this step, both the mutated and non-mutated DNA sequences are amplified, while the vast majority of wild type DNA remains in a very small proportion. The mutation is then detected by primer extension with incorporation of digoxigenin or biotin labeled nucleotide in the primer at the site of mutation. The extended primer can be detected by gel electrophoresis as a band migrating slower versus the control or by a standard chemiluminescence reaction with a commercial kit.

As a positive control, the DNA from two cancer cell lines known to contain mutations in P53 gene, were used: the ovarian line TOV-112D containing a mutation in codon 175 and lung cancer line CRL-5818 with a mutation in codon 273. They were purchased from ATCC. The cells were expanded in culture and DNA prepared from cells at our request at ATCC. With this strategy, it was possible to detect mutations when tumor cell DNA was diluted $10^{18}$ in normal DNA. The method was set up initially for codon 175 mutation of P53 gene where a G is mutated and replaced by A (CGC wild codon>CAC mutated codon). Later, a similar strategy was used to set the protocols for p53 mutations in codon 273 and K ras gene mutation in codon 12.

Materials and Methods

The primers for PCR amplification of 240 by genomic fragment surrounding the mutation were taken from literature. The primers for extension were selected by us from gene sequences available in data base.

All the primers were synthesized by Bioneer and Sigma Companies, at our request.

Two polymerases for PCR and primer extension in our experiments, were AccuPrime Supermixl from Invitrogen and Deep Vent DNA Polymerase from NE BioLabs. Vent polymerase has a high fidelity and is especially effective for reading GC rich sequences. For prime extension, the best results were obtained with AmpliTaq® Gold DNA Polymerase (Taq polymerase—available from Applied Biosystems, Grand Island, N.Y.).

The samples of serum were collected from patients with cancer in various stages according to the IRB approved protocol at our institution.

Isolation of DNA for Serum

Several methods of DNA purification from blood have been tested, but the following two procedures provided us with the best results.

V1 procedure uses QIAmp blood DNA midi kit Cat #51183 from Qiagen. This included passing 0.5 ml serum through a column with a resin that absorbs only the DNA. After washing the column, the DNA is eluted in water and can be used directly in PCR reaction.

V2 included in whole genome amplification of DNA from 1.5 ul serum using the kit REFLI ultrafast kit from Qiagen. This procedure amplifies by about 700-fold the whole genomic DNA from serum or blood cells in 90 minutes with uniform representation of all sequences. It is based on isothermal Multiple Displacement Amplification.

PCR Amplification 2 ul from an initial amplification step was then PCR-amplified by nested primer. The initial amplification was carried out with primers selected from exons 5 and 6 of p53 gene. Forward primer: 5'-tctgtctttgctgcctcttct-3' (SEQ ID NO: 1) and reverse 5'-agagcaatcagtgaggaatcag (SEQ ID NO: 2).

PCR reaction was run in 0.5 mM of each dNTP, 200 pmol of each primer and one unit Deep Vent DNA Polymerase, (NE Biolabs) 1× enzyme buffer in 20 ul volume. The program included an initial 4 min at 95° C. followed by 30 cycles of heating at 95° C. for 1 min, annealing at 65° C. for 30 sec and at 68° C. for AccuPrime and 72° C. for Vent with a final extension of 4 min at 68° C. or 72° C. The amplification generated a fragment of 280 bp as expected. The second round of amplification was carried out with 2 ul of the dilution 1:100 from first round, for 30 cycles in the same conditions except the primers were: forward 5'-ccttcctcttcctacagtact-3' (SEQ ID NO: 3) and reverse 5'-gaatcagtgaggaatcagag-3' (SEQ ID NO: 4).

The purification of the PCR product of primers and unused dNTP should be performed on a Qiagen column, or alternatively the PCR product could be treated with 10 units of antartic phosphatase and 40 units of exonuclease I (coli) for 30 minute at 37° C. followed by enzyme inactivation at 80° C. for 20 minutes.

Primer Extension (PE)

Stretches of 25-30 nucleotides upstream of the mutation side were selected from genomic sequence available in database. The terminal nucleotide of PE was complementary to substituted nucleotide at the side of the mutation (FIGS. 1A-B). The extension primer is extended (small letters), when encodes the mutated nucleotide (FIG. 1A), but does not extend when hybridized to wild type sequence (FIG. 1B).

A typical extension reaction includes 6 ul from PCR product 1 unit AmpliTaq® Gold DNA Polymerase (Taq polymerase), 3 ul extension primer for mutation in conc 0.1 micromole and 1 nanomole biotin dATP in 20 ul Vent pol buffer. The reaction is run for 50 cycles with the program 95° C. for 1 min, 30 sec at 67° C., and at 72²C for 30 sec. Then, 10 ul are run in a Lonza gel together a reaction with extension primer for wild sequence. A significant delay in migration of the product of mutated extended primer can be noticed due to incorporation of biotinylated nucleotide. Alternatively, the whole product of extension can be dot blotted and after drying and washings, the incorporated biotin could be detected by chemiluminescence using a commercial kit (Roche).

Alternatively to Amplitaq® Gold DNA Polymerase, any polymerase can be used for mutation detection, if a blocking primer is added to the extension reaction. A blocking primer is an extension primer, which terminates at 3' end with a dideoxynucleotide triphosphate (ddNTP), complementary to the wild nucleotide (FIG. 2).

With at least 20-fold molar excess relative to the regular extension primer (concentration ratio of 1:20 of regular extension primer: blocking polymer), and in the presence of any polymerase, the blocking primer will interfere with extension of non-mutated primer, but will allow only the expansion of mutated primer (FIG. 1A).

This fragment can be additionally PCR amplified with a selected primer, extending upstream the 5' extremity of extension primer ("tail") and a primer selected from gene sequence close to fragment 3' terminus. Amplification preferably uses 6 ul from PE reaction for 50 cycles using these primers and Vent polymerase and results in a single fragment of expected size. This fragment, when purified by gel electrophoresis and sequenced with "tail" primer, will reveal the expected mutation. The sequence should be generated with "tail" primer, and include the extension primer, the mutation site, and a portion of gene sequence downstream of mutation.

The "tail" primer used for PCR was: 5'-TGCACGAGGATGCTATCAAGG-3' (FIG. 3—SEQ ID NO: 10), which was a part of extension primer at 5' end.

Results

PE-PCR combines several molecular biology procedure in a novel simple and very sensitive strategy for detection of known mutations in blood cell free DNA, which can be performed in one to two days, or less. The PE-PCR method can be used in two versions according to the required level of sensitivity.

Version 1 includes purification of blood DNA by V1, one round of PCR for 30 cycles, and primer extension with reading in the gel. This version can provide genetic information for most required studies.

Version 2 includes whole gene amplification of blood DNA, followed by two rounds of PCR amplification and primer extension with reading by chemiluminescence. This is able to detect mutated DNA in dilution of $10^{18}$. That is intended appropriately for use for early detection of cancer.

Blood from 28 patients with lung, colon and pancreatic cancers were tested for presence of mutations in p 53 gene codons 175 and 237 and K ras gene codon 12. In 12 patients, a mutation in one of these genes was detected. In two of these patients, the same mutation was identified commercially in the primary tumors.

Potential applications of present PE-PCR technology presented herein, include:

The detection of mutations in EGFR, ras, braf and other genes useful for determining the response of certain targeted therapy. This will overcome the short supply of biopsy tissue for testing in certain patients and will benefit these patients of this therapy.

The early detection of tumor recurrence after tentative curative treatment with surgery or radiation. In these patients, detection of microscopic disease by PE-PCR could allow the systemic chemotherapy to cure some of them similarly with adjuvant chemotherapy in patients with LN involvement.

Preliminary studies with other technologies for mutation detections in blood DNA indicate that these abnormalities can be found long before the tumors are detectable clinically. If this finding were confirmed with PE-PCR, it would be possible that after detection of blood DNA mutations indicating the presence of a malignancy, the patient will be followed at short interval with whole body PET scan until a small lesion is detected in his/her body. After lesion biopsy, the patient can be eventually cured by surgical resection.

As a research tool to explore non-invasively the dynamics of molecular alterations during carcinogenesis and the effect of various environmental factors or therapeutic agents.

While this invention has been described as having preferred sequences, ranges, steps, order of steps, materials, structures, shapes, configurations, features, components, or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

What is claimed is:

1. A method of detecting mutation in blood cell-free DNA, comprising the steps of:
   a) providing a serum sample;
   b) isolating DNA from the serum sample;
   c) amplifying the DNA by polymerase chain reaction (PCR) by using at least one forward primer as set forth in SEQ ID NO: 1;
   d) subjecting the reaction product of step c) to primer extension (PE); and
   e) separating the reaction product of step d) and identifying the mutation by gel electrophoresis.

2. The method of claim 1, wherein:
the step c) is carried out for 30 cycles.

3. The method of claim 1, wherein:
the step c) is carried out by using at least one reverse primer as set forth in SEQ ID NO: 2.

4. The method of claim 2, wherein:
the step c) is carried out on mutated DNA fragments.

5. The method of claim 1, wherein:
the step b) is carried out by passing the serum through a column with a resin absorbing only the DNA.

6. The method of claim 1, wherein:
the step d) is carried out in the presence of Taq polymerase for 50 cycles.

7. A method of detecting mutation in blood cell-free DNA, comprising the steps of:
a) providing a serum sample;
b) subjecting the serum sample to whole genome DNA amplification;
c) amplifying the DNA of step b) by a first polymerase chain reaction (PCR) by using at least one forward primer as set forth in SEQ ID NO: 1;
d) re-amplifying a portion of the reaction product of step c) by a second polymerase chain reaction (PCR);
e) subjecting the reaction product of step d) to primer extension (PE); and
f) separating the reaction product of step e) and identifying mutation by gel electrophoresis or chemiluminescence.

8. The method of claim 7, wherein:
the step c) is carried out for 30 cycles.

9. The method of claim 7, wherein:
The step c) is carried out by using at least one reverse primer as set forth in SEQ ID NO: 2.

10. The method of claim 9, wherein:
the step d) is carried out for 30 cycles.

11. The method of claim 10, wherein:
the step d) is carried out by using at least one nested primer.

12. The method of claim 10, wherein:
the step d) is carried out by using at least one forward primer as set forth in SEQ ID NO: 3.

13. The method of claim 12, wherein:
the step d) is carried out by using at least reverse primer as set forth in SEQ ID NO: 4.

14. The method of claim 11, wherein:
the portion in step d) comprises the reaction product of step c) diluted by a ratio of 1:100.

15. The method of claim 7, wherein:
the step c) is carried out on mutated DNA fragments.

16. The method of claim 7, wherein:
the step e) is carried out in the presence of Taq polymerase for 50 cycles.

17. A method of detecting mutation in blood cell-free DNA, comprising the steps of:
a) providing a serum sample;
b) isolating DNA from the serum sample;
c) amplifying the DNA by polymerase chain reaction (PCR) by using at least one forward primer as set forth in SEQ ID NO: 1, and at least one reverse primer as set forth in SEQ ID NO: 2;
d) subjecting the reaction product of step c) to primer extension (PE) by using at least one blocking primer as set forth in SEQ ID NO: 9 and an extension primer; and
e) separating the reaction product of step d) and identifying the mutation by gel electrophoresis.

18. The method of claim 17, wherein:
the concentration of the blocking primer is 20-fold of the extension primer.

19. The method of claim 17, wherein:
the reaction product of step d) is further PCR amplified prior to the separation step e), by using a primer as set forth in SEQ ID NO: 10.

20. The method of claim 17, wherein:
the reaction product of step c) is re-amplified prior to step d), by a second polymerase reaction (PCR), by using at least one forward primer as set forth in SEQ ID NO: 3, and at least one reverse primer as set forth in SEQ ID NO: 4.

21. A method of detecting mutation in blood cell-free DNA, comprising the steps of:
a) providing a serum sample;
b) subjecting the serum sample to whole genome DNA amplification;
c) amplifying the DNA of step b) by a first polymerase chain reaction (PCR);
d) re-amplifying a portion of the reaction product of step c) by a second polymerase chain reaction (PCR) by using at least one reverse primer as set forth in SEQ ID NO: 4;
e) subjecting the reaction product of step d) to primer extension (PE); and
f) separating the reaction product of step e) and identifying mutation by gel electrophoresis or chemiluminescence.

22. A method of detecting mutation in blood cell-free DNA, comprising the steps of:
a) providing a serum sample;
b) isolating DNA from the serum sample;
c) amplifying the DNA by polymerase chain reaction (PCR);
d) subjecting the reaction product of step c) to primer extension (PE) by using at least one blocking primer as set forth in SEQ ID NO: 9 and an extension primer;
e) further PCR amplifying the reaction product of step d) by using a primer as set forth in SEQ ID NO: 10; and
f) separating the reaction product of step e) and identifying the mutation by gel electrophoresis.

23. A method of detecting mutation in blood cell-free DNA, comprising the steps of:
a) providing a serum sample;
b) isolating DNA from the serum sample;
c) amplifying the DNA by polymerase chain reaction (PCR);
d) re-amplifying the reaction product of step c) by a second polymerase reaction (PCR), by using at least one forward primer as set forth in SEQ ID NO: 3, and at least one reverse primer as set forth in SEQ ID NO: 4;
e) subjecting the reaction product of step d) to primer extension (PE) by using at least one blocking primer as set forth in SEQ ID NO: 9 and an extension primer; and
f) separating the reaction product of step e) and identifying the mutation by gel electrophoresis.

* * * * *